United States Patent [19] [11] Patent Number: 4,999,010
Mattson et al. [45] Date of Patent: Mar. 12, 1991

[54] DUAL BEAM OPTICAL NULLING INTERFEROMETRIC SPECTROMETER

[75] Inventors: David R. Mattson, Maple Bluff; Joel Covey; Stephen Weibel, both of Madison, Wis.

[73] Assignee: Mattson Instruments, Inc., Madison, Wis.

[21] Appl. No.: 388,646

[22] Filed: Jul. 31, 1989

[51] Int. Cl.⁵ .............................................. G01B 9/02
[52] U.S. Cl. ...................................................... 356/346
[58] Field of Search ........................................ 356/346

[56] References Cited

U.S. PATENT DOCUMENTS 2,571,937 10/1951 Peck ...................................... 356/346
3,753,619 8/1973 Thorpe et al. ....................... 356/346

OTHER PUBLICATIONS

Dual-Beam Fourier Transform Infrared Spectrometer, Koehcetal, Analytical Chemestry, 3-1978, pp. 418-422.
A New Version of a Michelson Interferometer FTIR Spectroscopy, Genzel et al., Infrared Physics, 1978, pp. 113-120.

Primary Examiner—Samuel Turner
Attorney, Agent, or Firm—Emrich and Dithmar

[57] ABSTRACT

A dual beam Fourier transform spectrometer produces two beams from a single infrared (IR) source. The beams are directed through a sample region, with one beam transiting a sample and the other beam transiting a reference cell. The sample and reference beams are then directed to a Michelson interferometer with cube corner retroflectors for optically cancelling the background signal from the separate sample and reference beams and for optically combining the sample and reference beams in an optically accurate and stable manner. The single combined beam, which contains the difference interferogram is directed to a single detector.

20 Claims, 1 Drawing Sheet

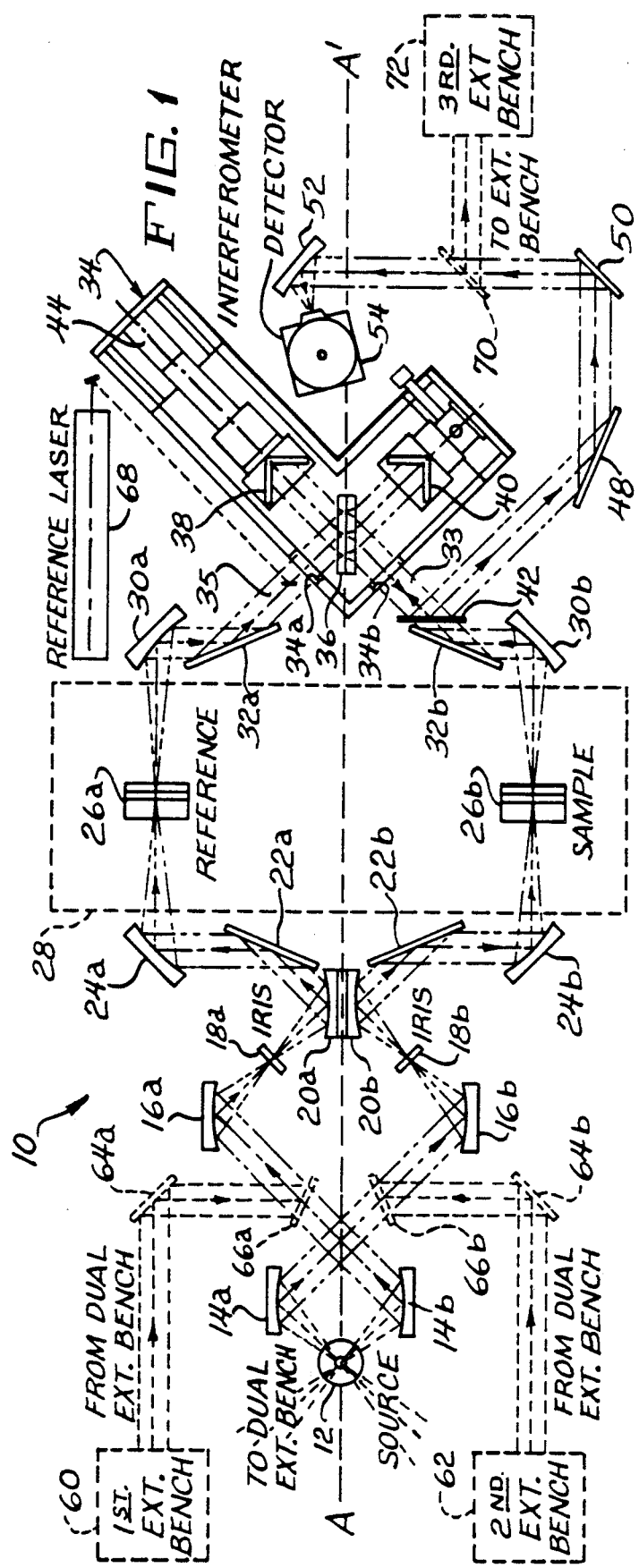
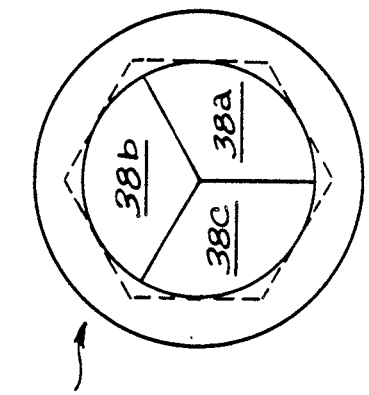
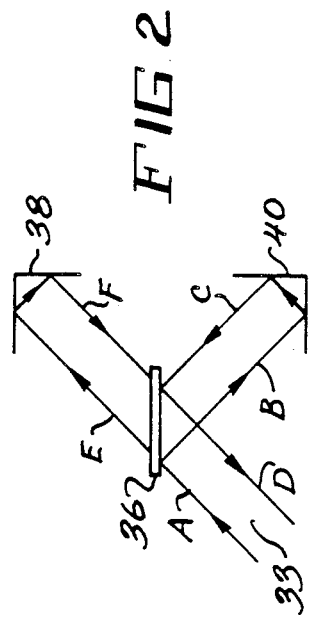

DUAL BEAM OPTICAL NULLING INTERFEROMETRIC SPECTROMETER

BACKGROUND OF THE INVENTION

This invention relates generally to the spectral analysis of the composition of materials and is particularly directed to Fourier transform infrared (FTIR) spectroscopy and related methods and apparatus.

Spectroscopic measurements generally involve the measurement of two spectra, a sample and a reference. The reference measurement is required to accurately record the spectroscopic response of the spectrometer and perhaps the response of a reference cell or control sample. In simplest form, a "single beam" approach is used. The reference spectrum is recorded followed by recording of the sample spectrum. The spectrum of the sample is derived by ratioing the sample spectrum to the reference spectrum in providing a transmittance spectrum of the sample with all instrument response characteristics removed.

The single beam approach has several intrinsic disadvantages. For example, the spectrometer's optical alignment may drift during the interval between the sample and reference measurements. Also, the atmosphere within the instrument may change between the sample and reference measurements. This frequently results in a water and carbon dioxide spectrum being superimposed upon the sample spectrum. Because water and carbon dioxide are strong infrared absorbers, this is a significant and frequent problem in infrared (IR) spectroscopic measurements. It is therefore desirable to minimize the time between the sample and reference measurements or to eliminate this time interval, if possible.

Sensor and other electronics limitations are another intrinsic disadvantage of the single beam approach. For example, in FTIR measurements, the amplitude of the reference signal is very large while the actual sample spectrum is typically provided in a very weak component of the strong background signal. This is an especially serious problem in FTIR because the interferogram of the reference spectrum which is recorded is a very large signal. The typical dynamic range of a sample spectrum signal within the interferogram is one part in a million, or smaller. This dynamic range generally exceeds the signal-to-noise ratio sensitivity of the FTIR measuring equipment. It is also difficult to maintain detectors as well as interferometer electronics linear over the wide dynamic range required to accurately measure the sample and reference interferograms. System nonlinearities limit the capability of such single beam spectrometers to provide highly accurate quantitative measurements. Finally, the sensitivity of many FTIR measurements is limited by the dynamic range of the detector preamplifier as well as the dynamic range of the analog-to-digital converter. Failure to remove the large background signal from the small digital signal results in amplification and other processing of both signals so as to reduce the accuracy of the sample spectrum measurement.

The dynamic range problem is far more critical in the FTIR measurement than in the dispersive measurement. The interferogram, i.e., the Fourier transform of the spectrum, is the measured signal in the Fourier transform spectrometer. The interferogram has a much larger dynamic range than the spectrum. Typical measurements might require detecting a 1% sample spectrum, i.e., one part in one hundred. However, the sample feature in the interferogram is frequently on the order of one part in one hundred thousand.

Current dispersive spectrometer designs generally make use of a dual beam arrangement employing a "chopper" to sample first the sample beam and then the reference beam. The chopper alternates between the beams at about 30 to 60 times per second so as to place a small alternating sample signal on the large background reference signal. By locking in on the AC component of the detector output so as to filter out the large DC background component, the sample spectrum may be measured more accurately. This technique is in widespread use in spectrometer designs and is generally referred to as the "dual beam" spectrometer in contrast to the "single beam" spectrometer.

Fourier transform, or interferometric spectroscopy, in general has not been amenable to the "chopper" dual beam design. Most of the problems arise from the interferometric principle of measuring all frequencies simultaneously. Each optical frequency has its own modulated audio frequency component in the interferogram. If a chopper is used, a doubly modulated signal is generated. These two modulations must be at distinct frequencies in order to be separated. This generally requires the chopper frequency to be on the order of 50 to 100 kHz, which is too fast to generate mechanically. The double modulation approach has been applied to polarization measurements, where the polarization can be alternated at these high frequencies. Because of these design issues, FTIR has remained a "single beam" technique with all its inherent problems. FTIR spectrometers have been designed with separate sample and reference beams and frequently employ switching mirrors to allow the system to alternate in successive scans between the two beams. The switching typically requires a few seconds and the scan times are limited to a few seconds, with several scans in each beam taken alternately. This approach removes some of the long term spectrometer drift effects, but does not address the dynamic range problems discussed above. Although such FTIR systems have been marketed as "dual beam" spectrometers, they are not in fact dual beam systems.

It is inherent in interferometer designs that two beams with the interferogram modulation signal are generated. One beam is generally available for the sample measurement and one beam returns to the IR source and is thus not available for spectroscopic use. If flat mirrors are employed in the interferometer, the beam returning to the source is spatially superimposed on the incoming source beam. The interferogram signal on the beam that returns to the source is an exact complement of the interferogram signal that emanates from the other interferometer port such that when one signal goes positive, the other goes negative by the same amount. This effect can be deduced from the conservation of energy principle applied at the interferometer's beamsplitter. Because the interferometer neither generates nor absorbs energy, allowing one of these beams to pass through a reference and the other to pass through a sample, a difference signal could be measured directly because the two interferograms would exactly cancel except for the small difference presented by the sample. Efforts have been made in the past to harness both the beamsplitter transmitted and reflected beams to provide a dual beam capability in the spectrometer. Such efforts have met with only limited success.

One prior approach at a dual beam FTIR spectrometer involves the slight misalignment of a "flat mirror" interferometer to spatially separate the incoming radiation beam from the interferometer return beam. Because this misalignment cannot be stabilized, the two interferograms do not cancel in a reproducible manner. The availability of cube corner retroflectors in the early 1980s of sufficient accuracy for use in FTIR interferometers gave rise to other attempts at developing a dual beam spectrometer. A cube corner interferometer allows the incoming radiation beam to be spatially separated from the beam that returns to the source. Thus, rays that enter the bottom of a cube corner interferometer leave from the top and vice versa. With the incoming radiation entering the lower portion of the interferometer, the two radiation beams emanating from the upper half of the interferometer may be used for spectroscopic measurements. This arrangement provides two interferograms which are spatially separated, one that can be passed through a sample and the other through a reference path. The two inteferograms are 180° out of phase and if properly combined will cancel the large background signal, leaving the small sample signal.

Various attempts have been made to construct such a dual beam spectrometer, but they have encountered a problem which limits their practicality. This problem arises from the inability to recombine two beams with sufficient precision. It has proven to be extremely difficult to bring the two separate beams back together in an optically precise manner. Not only have attempts to optically recombine the beams been unsuccessful, but attempts to electronically recombine electrical signals representing the beams in the detector and its associated electronics have also met with only limited success.

The present invention overcomes the aforementioned problems encountered in the prior art by providing a dual beam Fourier transform spectrometer wherein the source and detector locations in a conventional spectrometer are interchanged and which employs a Michelson interferometer with cube corner retroreflectors. Two beams generated from a single IR source are respectively directed through a sample and a reference and are subsequently combined into one beam containing a difference interferogram which is directed to a single detector.

OBJECTS AND SUMMARY OF THE INVENTION

Accordingly, it is an object of the present invention to provide an improved dual beam spectrometer which affords a high degree of measurement sensitivity and photometric accuracy as well as long term operating stability.

It is another object of the present invention to provide a dual beam spectrometer in which the sample and reference interferograms cancel so as to essentially eliminate residuals leaving only the difference interferogram for analysis.

Yet another object of the present invention is to simultaneously measure and compare in real time the interferograms of a sample and a reference.

A further object of the present invention is to provide a dual beam spectrometer wherein the two beams are recombined within the spectrometer's interferometer rather than at the detector.

A still further object of the present invention is to provide a dual beam spectrometer which requires only one interferogram measurement rather than the usual two for each sample for essentially halving the measurement time.

Another object of the present invention is to provide a dual beam Fourier transform, infrared spectrometer which employs currently available components and is particularly adapted for large scale, economical production using conventional manufacturing techniques.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is a simplified schematic diagram of a dual beam spectrometer in accordance with a preferred embodiment of the present invention;

FIG. 2 is a ray diagram illustrating the manner in which the sample beam is transmitted and reflected in the spectrometer's interferometer; and FIG. 3 is a planar view of a cube corner retroreflector used in a preferred embodiment of the present invention.

DESCRIPTION OF THE PREFERRED EMBODIMENT

Referring to FIG. 1, there is shown a schematic diagram of a dual beam spectrometer 10 in accordance with the principles of the present invention. The dual beam spectrometer 10 includes a point source of IR radiation 12. The IR point source 12 directs the radiation 360° about itself and onto a first pair of 90° off-axis paraboloid reflectors 14a and 14b. The paraboloid reflectors 14a, 14b are precisely matched and are symmetrically positioned with respect to an axis of symmetry A—A' through the dual beam spectrometer 10. The pair of paraboloid reflectors 14a, 14b, as well as all other reflectors in the dual beam spectrometer 10 discussed below, are preferably formed in a conventional manner using a diamond turn milling machine (not shown). Each of the first pair of paraboloid reflectors 14a, 14b forms a respective collimated beam of the IR radiation emanating from the point source 12 and directs a beam onto a respective one of a second pair of 90° off-axis paraboloid reflectors 16a and 16b. Thus, each of the first pair of paraboloid reflectors 14a, 14b takes a respective cone-shaped beam emanating from the point source 12 and collimates the beam. Paraboloid reflector 14a reflects a collimated IR beam onto paraboloid reflector 16b, while reflector 14b reflects a collimated beam onto reflector 16a. Each of the second pair of paraboloid reflectors 16a, 16b focuses and directs a respective one of the beams through a respective iris 18a, 18b and onto one of a third pair of 90° off-axis paraboloid reflectors 20a and 20b. Each of the irises 18a and 18b includes a respective aperture through which an IR beam is reflected by one of the second pair of paraboloid reflectors 16a, 16b. The aperture in each of the irises can be varied in order to control the throughput, or amount of IR beam energy, in the dual beam spectrometer 10. Each of the beams reflected by the second pair of paraboloid reflectors 16a, 16b is focused generally at the aperture of its associated iris 18a, 18b.

The third pair of paraboloid reflectors 20a, 20b are positioned in a back-to-back arrangement generally along the axis of symmetry A—A'. Paraboloid reflectors 20a and 20b re-collimate the beams respectively focused by the second pair of paraboloid reflectors 16a, 16b and direct the thus collimated beams onto planar reflectors 22a and 22b, from which the collimated beams are further reflected onto a respective one of a fourth pair of paraboloid reflectors 24a and 24b. Each of the fourth pair of paraboloid reflectors 24a, 24b focuses a respective one of the IR beams and directs the beam into a sample compartment 28, shown in dotted line form in FIG. 1. The sample compartment 28 includes a reference cell 26a as well as a sample cell 26b containing a sample of the material under investigation. The reference cell 26a contains a known substance and is used to generate a reference spectrum with which the sample spectrum is compared as described below.

After transiting the reference cell 26a, the reference beam 35 is re-collimated by means of paraboloid reflector 30a which reflects the reference beam onto a planar reflector 32a. Likewise, the sample beam 33 is recollimated by means of a paraboloid reflector 30b and is reflected onto a planar reflector 32b. The planar reflectors 32a, 32b respectively direct the collimated reference and sample beams to an interferometer 34.

The interferometer 34 is preferably a cube corner Michelson interferometer which optically cancels the background signal from the separate sample and reference beams as described in the following paragraphs. As shown in FIG. 1, the axis of symmetry A—A' of the dual beam spectrometer 10 is defined by matching pairs of paraboloid and planar reflectors spaced on respective sides of this axis. Each of the collimated beams formed by a respective one of the first pair of paraboloid reflectors 14a, 14b is thereafter separated from the other beam by the aforementioned combination of paraboloid and planar reflectors until the two beams are combined in the interferometer 34 as described below.

The interferometer 34 includes a beamsplitter 36 onto which the reference and sample beams 35, 33 are directed through respective apertures 34a and 34b in the interferometer. The beamsplitter 36 is conventional in design and operation and is typically comprised of a potassium bromide substrate upon which is deposited a germanium coating on facing surfaces thereof. The germanium coating serves as a pure dielectric in transmitting one half and reflecting the other half of the incident beam without absorbing any of the incident radiation. One half of each of the sample and reference beams 33, 35 is transmitted while the remaining half of each of these beams is reflected by the beamsplitter 36. The interferometer 34 further includes first and second cube corner retroflectors 38 and 40. The first cube corner retroreflector 38 is positioned so as to receive and reflect one half of the sample beam 33 transmitted through the beamsplitter 36 and one half of the reference beam 35 reflected by the beamsplitter. Similarly, the second cube corner retroreflector 40 is positioned so as to reflect half of the sample beam 33 which is reflected by the beamsplitter 36 and half of the reference beam 35 which is transmitted by the beamsplitter.

Each of the first and second cube corner retroreflectors 38, 40 is conventional in design and operation and includes three planar reflectors joined in an edge-to-edge manner so as to form the inner corner of a cube. Details of the first cube corner retroreflector 38 are shown in the planar view of FIG. 3. The first cube corner retroreflector 38 includes first, second and third planar reflectors 38a, 38b and 38c joined and continuous along adjacent edges so as to form a unitary reflecting element. The cube corner retroreflectors 38, 40 have the characteristic that a beam incident on a lower portion of the reflector is reflected back in the opposite direction from a corresponding upper portion of the reflector. Thus, the incident and reflected beams are displaced an equal distance from a median plane passing through the corner defined by the intersection of the three planar reflectors which comprise the cube corner retroreflector. This characteristic of cube corner retroreflectors will now be further described with respect to FIG. 2.

FIG. 2 is a simplified ray diagram illustrating the incidence of a sample beam 33 upon the beamsplitter 36. In FIG. 2, ray A represents a ray incident on the lower half of the beamsplitter 36 such that one half of ray A is transmitted via the beamsplitter as ray E to a lower portion of the first cube corner retroreflector 38, while one half of ray A is reflected by the beamsplitter to a lower half portion of the second cube corner reflector 40 as represented by ray B. Transmitted ray E is reflected from a lower half portion of the first cube corner retroreflector 38 to an upper portion thereof lying above a plane passing through the corner of the retroreflector. Similarly, ray B which is incident upon a lower half of the second cube corner retroreflector 40 is reflected upward to the upper half portion of the retroreflector and is further reflected back as ray C. One half of ray C is reflected by the beamsplitter 36, while one half of ray F is transmitted by the beamsplitter such that these two rays combine to form reflected ray D which is anti-parallel to the incident ray A and is directed outward from an upper portion of the beamsplitter.

Therefore, by aligning planar reflectors 32a and 32b with lower portions of the first and second cube corner retroreflectors 38, 40, the sample and reference beams 33, 35 are incident upon respective lower portions of the retroreflectors and are reflected by the retroreflectors and exit the interferometer 34 at a position above the plane of the incident sample and reference beams. The combined sample and reference beams exit the interferometer 34 via the aperture 34b therein and are incident upon a planar reflector 42. The planar reflector 42 is located above the plane defined by the planar reflectors 32a and 32b as well as the pair of fifth paraboloid reflectors 30a and 30b and all of the aforementioned planar and paraboloid reflectors.

The sample and reference beams 33, 35 are complementary and shifted in phase by 180° as they are combined within the interferometer 34. This 180° phase shift arises from the manner in which the incident beams are transmitted and reflected by beamsplitter 36.

The collimated beam representing the combined sample and reference beams which exits the interferometer 34 via its second aperture 34b is reflected by the planar reflector 42 to a pair of aligned planar reflectors 48 and 50 and thence to a paraboloid reflector 52. The paraboloid reflector 52 focuses the collimated beam onto the sensor element of a detector 54. Thus, a pair of beams from a point source of radiation 12 are respectively passed through a sample and a reference and are then recombined in a cube corner retroreflector Michelson interferometer so as to produce a "nulled" interferogram resulting from phase cancellation. The interferometer 34 used in a preferred embodiment of the present dual beam spectrometer 10 is the Nova Cygni spectrometer, available from the assignee of the present application. The detector 54 used in a preferred embodiment is an infrared detector.

Another feature of the present invention makes use of a reference laser 68 for controlling the position, direction and velocity of the first cube corner retroreflector 38 in the interferometer 34. Coupled to the first cube corner retroreflector 38 is displacement means 44 such as an electric linear motor with appropriate linkage to the retroreflector. The displacement means 44 provides for the linear displacement of the first retroreflector 38 along the axis of the sample beam 33 permitting the interferometer 34 to sweep through selected data points in obtaining the spectrum of the sample in a conventional manner. The second cube corner retroreflector 40 is positioned in the interferometer 34 in a fixed, stationary manner.

The dual beam spectrometer 10 provides for additional testing and analysis capability as shown in FIG. 1. For example, first and second external test benches 60 and 62 may also be provided for receiving respective beams from the IR point source 12. The output beam from the first external test bench 60 may be provided to one of the second pair of paraboloid reflectors 16a via a planar reflector 64a and a planar reflector 66a. In this manner, the output beam from the first external test bench 60 may be either combined with or replace the reference beam. Similarly, the output of a second external test bench 62 may be provided to the other reflector 16b of the second pair of paraboloid reflectors via a planar reflector 64b and a planar reflector 66b. The output beam of the second external test bench 62 may thus replace the sample beam in either analyzing another sample or performing another analysis of the same sample. Similarly, the output beam may be provided via a planar reflector 70 to a third external test bench 72 to allow for additional analysis of the output sample beam by another infrared detector (not shown).

There has thus been shown a dual beam Fourier transform infrared spectrometer which employs a pair of beams derived from a single point source which are respectively directed through a sample and a reference for subsequent combination in producing a "nulled" interferogram resulting from phase cancellation. The dual beam spectrometer affords improved sensitivity, photometric accuracy, instrument stability, and requires an order of magnitude less measurement time than single beam acquisitions for spectra of comparable signal-to-noise ratio.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A spectrometer comprising:
   a source of radiant energy;
   first beam forming means for directing a first beam of said radiant energy on a reference sample in forming a first spectrum thereof, said first beam forming means including a first plurality of spaced reflectors;
   second beam forming means for directing a second beam of said radiant energy on a sample to be analyzed in forming a second spectrum thereof, said second beam forming means including a second plurality of spaced reflectors;
   interferometer means including a beamsplitter and cube corner retroflectors for combining said first and second beams after being respectively directed on said reference sample and said sample to be analyzed so as to form a third beam representing the difference between said first and second beams and containing an interferogram of said sample to be analyzed, wherein said spectrometer includes an axis of symmetry between said source and said interferometer means and wherein said first and second beam forming means are disposed on respective opposed sides of said axis of symmetry; and
   single detector means responsive to said third beam for detecting said interferogram.

2. The spectrometer of claim 1 wherein said first and second pluralities of spaced reflectors are equal in number and symmetrically positioned on respective sides of said axis of symmetry.

3. The spectrometer of claim 1 wherein said interferometer means includes optical means for causing said first and second beams to be 180° out of phase such that said third beam contains a nulled interferogram resulting from phase cancellation of said first and second beams.

4. The spectrometer of claim 3 wherein said optical means includes said beamsplitter in combination with first and second cube corner retroreflectors.

5. The spectrometer of claim 4 further comprising displacement means coupled to said first retroreflector for displacing said first retroreflector and allowing said interferometer means to sweep through selected data points in obtaining a spectrum of the sample to be analyzed.

6. The spectrometer of claim 4 wherein each of said retroreflectors reflects a beam incident from a first direction on a first portion of the retroreflector in a second opposed direction from a second opposed portion of the retroreflector.

7. The spectrometer of claim 1 further comprising reflecting means for reflecting said third beam to said detector means.

8. The spectrometer of claim 7 wherein said first and second pluralities of spaced reflectors lie in a common plane.

9. The spectrometer of claim 8 wherein said reflecting means is positioned in a spaced manner from said common plane.

10. The spectrometer of claim 9 wherein each of said first and second beam forming means includes respective variable aperture means for controlling the intensities of said first and second beams, respectively.

11. The spectrometer of claim 10 further comprising reflector means aligned with the second portion of said interferometer means for reflecting said third beam to said detector means.

12. A spectrometer comprising:
    a source of radiant energy;
    first beam forming means for directing a first beam of said radiant energy on a reference sample in forming a first spectrum thereof;

second beam forming means for directing a second beam of said radiant energy on a sample to be analyzed in forming a second spectrum thereof, wherein said first and second beam forming means lie in a single plane and define an axis of symmetry in the spectrometer with said source of radiant energy disposed on said axis of symmetry and said first and second beam forming means disposed on opposed sides of said axis of symmetry;

interferometer means including a beamsplitter for combining said first and second beams after being respectively directed on said reference sample and said sample to be analyzed so as to form a third beam representing the difference between said first and second beams and containing an interferogram of said sample to be analyzed, wherein said interferometer includes a first portion in said plane for receiving said first and second beams and a second portion disposed out of said plane for directing said third beam; and single detector means responsive to said third beam for detecting said interferogram.

13. A method for obtaining a spectrum of a sample with a spectrometer having a source and a detector or radiant energy, said method comprising the steps of:

forming a first beam of radiant energy of the source;

forming a second beam of radiant energy of the source, wherein said first and second beams are optically identical and are disposed on opposed sides of an axis of symmetry of the spectrometer and wherein the source of radiant energy is disposed on said axis of symmetry;

directing said first beam onto a reference so as to form a first spectrum;

directing said second beam onto a sample so as to form a second spectrum;

combining said first and second beams so as to cancel said first spectrum from said second spectrum in forming a third beam containing an interferogram of the sample; and directing said third beam to the detector for detecting said interferogram.

14. The method of claim 13 further comprising the step of controlling the intensities of said first and second beams.

15. The method of claim 13 wherein the step of combining said first and second beams includes reflecting each of said beams from a respective cube corner retroreflector after transmitting and reflecting portions of each beam by means of a beamsplitter.

16. The method of claim 15 further comprising the step of forming said first and second beams in a common plane and forming said third beam in spaced relation from said common plane.

17. The method of claim 13 further comprising the step of sweeping said third beam through a range of data points in obtaining a spectrum of the sample.

18. The method of claim 13 further comprising the step of directing said first and second beams respectively through said reference and said sample so as to form first and second absorption spectra.

19. The method of claim 13 wherein the step of forming said third beam includes rendering said first and second beams 180° out of phase such that said third beam contains a nulled interferogram resulting from phase cancellation of said first and second beams.

20. A spectrometer comprising:

first beam forming means for receiving a first cone-shaped beam of radiant energy from a point source radiating energy over a 360° solid angle and for collimating, focusing and directing said first beam onto a reference so as to form a first spectrum;

second beam forming means for receiving a second cone-shaped beam of radiant energy from said point source and for collimating, focusing and directing said second beam onto a sample so as to form a second spectrum;

interferometer means for receiving and combining said first and second beams so as to form a third beam representing the difference between said first and second beams and containing a nulled interferogram of the sample; and single detector means responsive to said third beam for detecting said interferogram.

* * * * *